US010371654B2

(12) United States Patent
Rapoport

(10) Patent No.: US 10,371,654 B2
(45) Date of Patent: *Aug. 6, 2019

(54) SYSTEM AND METHOD FOR A NONDESTRUCTIVE ON-LINE TESTING OF SAMPLES

(71) Applicant: Aspect AI Ltd., Shoham (IL)

(72) Inventor: Uri Rapoport, Moshav Ben Shemen (IL)

(73) Assignee: ASPECT AI LTD., Shoham (IL)

( * ) Notice: Subject to any disclaimer, the term of this patent is extended or adjusted under 35 U.S.C. 154(b) by 245 days.

This patent is subject to a terminal disclaimer.

(21) Appl. No.: 15/290,609

(22) Filed: Oct. 11, 2016

(65) Prior Publication Data

US 2017/0030846 A1 Feb. 2, 2017

Related U.S. Application Data

(63) Continuation of application No. 14/464,400, filed on Aug. 20, 2014, now Pat. No. 9,494,540, which is a (Continued)

(51) Int. Cl.
G01R 19/00 (2006.01)
G01N 24/08 (2006.01)
G01N 27/02 (2006.01)
G01N 22/04 (2006.01)
G01N 33/02 (2006.01)

(52) U.S. Cl.
CPC ........... *G01N 24/085* (2013.01); *G01N 22/04* (2013.01); *G01N 27/023* (2013.01); *G01N 33/02* (2013.01)

(58) Field of Classification Search
None
See application file for complete search history.

(56) References Cited

U.S. PATENT DOCUMENTS 1,449,996 A 3/1923 Hepperle
1,638,047 A 8/1927 Maclaren
(Continued)

FOREIGN PATENT DOCUMENTS

CN 1417588 5/2003
CN 201464391 5/2010
(Continued)

OTHER PUBLICATIONS

Bos, F., and S. Bos Casagrande. "On-line non-destructive evaluation and control of wood-based panels by vibration analysis." Journal of sound and vibration 268.2 (2003): pp. 403-412.
(Continued)

*Primary Examiner* — Vincent Q Nguyen
(74) *Attorney, Agent, or Firm* — Pearl Cohen Zedek Latzer Baratz LLP

(57) ABSTRACT

An MRI-free non-destructive on-line system for detecting a presence of a material in a sample. The system includes a flow conduit encompassed by a tunable RF coil and having an input duct and an output duct; a flow of the sample through the flow conduit; a signal detector that detects frequency-dependent output signals as a function of a frequency variation of the RF tunable coil within a frequency range of an RF resonant frequency of a standard sample of the substance; and a processing unit.

20 Claims, 7 Drawing Sheets

Related U.S. Application Data continuation-in-part of application No. 13/234,433, filed on Sep. 16, 2011, now Pat. No. 8,847,608, which is a continuation-in-part of application No. 12/377,980, filed as application No. PCT/IL2007/001043 on Aug. 21, 2007.

(60) Provisional application No. 60/838,887, filed on Aug. 21, 2006.

(56) References Cited

U.S. PATENT DOCUMENTS

| | | |
|---|---|---|
| 1,823,056 A | 9/1931 | Marburg |
| 2,004,134 A | 6/1935 | Ross |
| 2,679,990 A | 6/1954 | Mathzeit et al. |
| 2,709,555 A | 5/1955 | Schroder |
| 2,943,814 A | 7/1960 | Mittag et al. |
| 3,297,277 A | 1/1967 | MacKenzie |
| 3,689,833 A | 9/1972 | Hogg |
| 3,690,593 A | 9/1972 | Kettering |
| 3,907,231 A | 9/1975 | Kreiner |
| 3,911,731 A | 10/1975 | Walker et al. |
| 4,239,420 A | 12/1980 | Thibonnier et al. |
| 4,334,806 A | 6/1982 | Liu |
| 4,496,907 A | 1/1985 | Funk et al. |
| 4,568,225 A | 2/1986 | Alexandrov et al. |
| 5,035,231 A | 7/1991 | Kubokawa et al. |
| 5,166,620 A | 11/1992 | Panosh |
| 5,313,162 A | 5/1994 | De Graf et al. |
| 5,371,464 A | 12/1994 | Rapoport |
| 5,522,988 A | 6/1996 | Cortes et al. |
| 5,534,780 A | 7/1996 | Lilly |
| 5,562,591 A | 10/1996 | Marchand et al. |
| 5,862,060 A | 1/1999 | Murray, Jr. |
| 6,015,246 A | 1/2000 | Yamane et al. |
| 6,046,592 A | 4/2000 | Rathke et al. |
| 6,068,428 A | 5/2000 | Nair et al. |
| 6,103,934 A | 8/2000 | Hallinan et al. |
| 6,228,650 B1 | 5/2001 | Moore et al. |
| 6,395,538 B1 | 5/2002 | Naughton et al. |
| 6,401,519 B1 | 6/2002 | McFarland et al. |
| 6,603,993 B1 | 8/2003 | Coutts et al. |
| 6,979,308 B1 | 12/2005 | MacDonald et al. |
| 7,248,050 B2 | 7/2007 | Hofmann et al. |
| 7,740,424 B2 | 6/2010 | Pardini et al. |
| 7,807,419 B2 | 10/2010 | Hennessey et al. |
| 7,883,289 B2 | 2/2011 | Weisman |
| 8,101,383 B2 | 1/2012 | Henriksen et al. |
| 8,189,737 B2 | 5/2012 | Keller et al. |
| 8,851,018 B2 | 10/2014 | Rapoport et al. |
| 8,896,310 B2 | 11/2014 | Rapoport |
| 8,992,132 B2 | 3/2015 | Rapoport et al. |
| 2002/0010394 A1 | 1/2002 | Zavislan |
| 2003/0206020 A1 | 11/2003 | Cohen et al. |
| 2003/0210052 A1 | 11/2003 | Okada et al. |
| 2004/0090231 A1 | 5/2004 | Augustine et al. |
| 2005/0060868 A1 | 3/2005 | McMurtry |
| 2005/0116712 A1 | 6/2005 | Corver et al. |
| 2007/0091428 A1 | 4/2007 | Wilson et al. |
| 2008/0007262 A1 | 1/2008 | Yamauchi et al. |
| 2008/0068018 A1 | 3/2008 | Massin et al. |
| 2008/0111549 A1 | 5/2008 | Nabetani |
| 2008/0231277 A1 | 9/2008 | Yamamoto et al. |
| 2008/0260217 A1 | 10/2008 | Mashiach |
| 2009/0053777 A1 | 2/2009 | Hennessey et al. |
| 2009/0197294 A1 | 8/2009 | Rapoport |
| 2011/0162652 A1 | 7/2011 | Rapoport |
| 2011/0186049 A1 | 8/2011 | Rapoport |
| 2011/0234347 A1 | 9/2011 | Rapoport |
| 2011/0304333 A1 | 12/2011 | Rapoport |
| 2012/0005949 A1 | 1/2012 | Stevens et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0119742 A1 | 5/2012 | Rapoport |
| 2012/0212224 A1 | 8/2012 | Burns |
| 2013/0079624 A1 | 3/2013 | Rapoport |
| 2013/0109956 A1 | 5/2013 | Rapoport |
| 2013/0217074 A1 | 8/2013 | Sjoede et al. |
| 2013/0237803 A1 | 9/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2014/0050539 A1 | 2/2014 | Rapoport et al. |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0378821 A1 | 12/2014 | Rapoport et al. |
| 2014/0378825 A1 | 12/2014 | Rapoport et al. |
| 2015/0065788 A1 | 3/2015 | Rapoport |
| 2016/0077176 A1 | 3/2016 | Rabinovitz et al. |

FOREIGN PATENT DOCUMENTS

| | | |
|---|---|---|
| CN | 102288629 | 12/2011 |
| CN | 202267662 | 6/2012 |
| CN | 102954978 | 3/2013 |
| EP | 0730164 | 9/1996 |
| EP | 1102020 | 5/2001 |
| EP | 1500944 | 1/2005 |
| EP | 2551692 | 1/2013 |
| GB | 1518541 | 7/1978 |
| JP | 2009011652 | 1/2009 |
| WO | WO9744410 | 11/1997 |
| WO | WO02071050 | 9/2002 |
| WO | WO2007093992 | 8/2007 |
| WO | WO2008023370 | 2/2008 |

OTHER PUBLICATIONS

Robinson, David W. "Automatic fringe analysis with a computer image-processing system." Applied Optics 22.14 (1983): pp. 2169-2176.

Ndambi, J.-M., J. Vantomme, and K. Harri. "Damage assessment in reinforced concrete beams using eigenfrequencies and mode shape derivatives." Engineering Structures 24.4 (2002): pp. 501-515.

Nelson, Rick. "How does a Smith chart work?." Test & Measurement World Jul. 1, 2001: pp. 1-12.

International Search Report for PCT Application No. PCT/IL2007/01043 dated Oct. 20, 2008.

Office Action for U.S. Appl. No. 12/377,980 dated Feb. 4, 2011.

Final Office Action for U.S. Appl. No. 12/377,980 dated Mar. 17, 2011.

Office Action for U.S. Appl. No. 13/234,433 dated Mar. 11, 2011.

Notice of Allowance for U.S. Appl. No. 14/464,400 dated Jul. 6, 2016.

Alic et al., Facilitating Tumor Functional Assessment by Spatially Relating 3D Tumor Histology and in Vivo MRI: Image Registration Approach, Plos One, Aug. 2011, vol. 6, Issue 8, e22835 pp. 1-10.

Beutel et al. In situ sensor techniques in modern bioprocess monitoring, Appl. Microbiol Biotechnol (2011) 91:1493-1505.

Brecker et al., In situ proton-NMR analyses of *Escherichia coli* HB101 fermentations in $H_2O$ and in $D_2O$, Microbiology, 1999, 145, 3389-3397.

Castro et al., Performance trade-offs in in situ chemostat NMR, Biotechnol Prog. 1999, 185-195.

(56) References Cited

OTHER PUBLICATIONS

Levenson et al., Yield stress of pretreated corn stover suspensions using magnetic resonance imaging, Biotechnol. Bioeng. 2011;108:2312-2319.

Madabhushi et al., Automated detection of prostatic adenocarcinoma from high-resolution ex vivo MRI, IEEE Transactions on Medical Imaging, Dec. 2005, vol. 24, No. 12, 1611-1625.

Majors et al., NMR bioreactor development for live in-situ microbial functional analysis, Journal of Magnetic Resonance, 2008, 192, 159-166.

Meehan et al., Cultivator for NMR studies of suspended cell cultures, Biotechnology and Bioengineering, 1992, vol. 40, pp. 1359-1366.

Rapoport, URI, Preclinical imaging: the use of preclinical MRI characterization of disease progression and response to therapy, May 29, 2010, printed from website ArticleInput.com, 1-3.

Ruizhen et al., Observations of aerobic, growing *Escherichia coli* metabolism using an on-line nuclear magnetic resonance spectroscopy system, Biotechnology and Bioengineering, 1993, vol. 42, pp. 215-221.

Sarazin et al., NMR on-line monitoring of esterification catalyzed by cutinase, Biotechnology and Bioengineering, 1995, vol. 51, pp. 836-844.

Scheper et al., Fermentation monitoring and process control, Current Opinion in Biotechnology, 1994, 5:187-191.

SYSTEM AND METHOD FOR A NONDESTRUCTIVE ON-LINE TESTING OF SAMPLES

CROSS-REFERENCE TO RELATED APPLICATIONS

This application is a continuation of U.S. patent application Ser. No. 14/464,400, filed on Aug. 20, 2014, which is a continuation-in-part of U.S. patent application Ser. No. 13/234,433, filed Sep. 16, 2011, which is a continuation-in-part of U.S. patent application Ser. No. 12/377,980, now abandoned which is the National Stage of International Application No. PCT/IL2007/001043, filed Aug. 21, 2007, which claimed the benefit of U.S. Provisional Patent Application No. 60/838,887, filed Aug. 21, 2009, all of which are incorporated herein by reference in their entireties.

FIELD OF THE INVENTION

The present invention relates to MRI-based and alternatively to MRI-free systems and a method for nondestructive on-line testing of a sample of a substance by means of an MRI device generating RF frequency-dependent MRI (or MRI-free) signals. The MRI (or MRI-free) signals are processed and analyzed to optimize and improve the production process of the substance.

BACKGROUND OF THE INVENTION

The following prior art is believed to be the current status of the art:

U.S. Pat. No. 6,401,519 describes an improved system for measuring off-line characteristics of fluids.

Chinese Patent No. 1,417,588 describes an on-line water quality monitoring network system including an on-line monitoring instrument comprising physical parameter sensor, chemical pollutant density analyzer and in-situ flow meter.

U.S. Pat. No. 5,522,988 describes an on-line coupled liquid and gas chromatography system with an interface capillary tube interposed between a pair of capillary chromatographic columns.

EP 0730 164 A1 describes an MRI apparatus and method for nondestructive quality assessment and analysis of a sample, such as an unmilled rice grain and an unhulled rice seed. The sproutability of the rice seed and rice grain are determined from the MRI analysis of the food products.

The prior art references do not describe systems and/or methods for optimizing and improving industrial production processes, for industries such as the food production industry, by on-line nondestructive systems and methods.

Thus, there is an unmet need for on-line nondestructive systems and methods for controlling industrial production processes.

SUMMARY OF THE INVENTION

MRI-Based Non-Destructive On-Line System

The present invention relates to systems and a method for on-line nondestructive monitoring of a sample of a substance by introducing the sample into an MRI device and generating RF frequency-dependent MRI signals within a frequency range of the resonant frequency of the substance. The generated MRI signals are processed and analyzed to optimize and improve the production process of the substance by determining therefrom, reactances and inductances of samples of substances.

In the present invention, the RF frequency of the tunable RF coil of the MRI device generates MRI RF signals which are detected and processed, as known in the art. By means of Smith Curve software codes, the frequency-dependent reactances and inductances of samples of substances are determined. Frequency difference curves are generated and the amount of water, for example, found in the sample is determined.

Thus, using the present invention in a food production industry, it is possible to determine the quality of the substance undergoing examination, for example, by determining the relative amount of water contained in the sample. It is known in the art, that an MRI signal generated by a substance is dependent on the number of protons in the sample. Therefore, the MRI signal is dependent on the amount of water contained in the sample of the substance. Thus, a sample which includes an amount of water which is greater than a standard sample of the substance, generates a larger MRI RF signal than that which is generated by a standard sample. This is beneficial to the food industry.

Using the present invention it is possible to check the contents of a sample of a substance, such as an amount of water in a food product, by using an MRI device and the relevant peripheral devices, as described hereinbelow. Therefore, using the present invention it is possible to ascertain and check if a food product, for example, fulfills the statutory contents' requirements.

In addition, the present invention is configured for optimizing a production process of a substance by ensuring that the production process fulfills requisite requirements. For example, in the food industry, it is possible to check additional contents of the food products, such an acidity parameter in the food product as well as the amount of water contained in the food.

Furthermore, the present invention is adapted to measure and control water pollution by examining the MRI signals from water contaminant, such as an organic contaminant and/or an inorganic contaminant.

In the present invention, the sample to be tested is in a fluid state or in a solid state.

The non-destructive on-line system of the present invention is also adaptable for detecting a presence of at least one material and a characteristic of the material, such as the size of microns (e.g., 0.1 to 10 μm, 10-100 μm, 100 to, 500 μm), millimeters and centimeters, predefined size distribution and particles shape, $A_w$ water content and any combination thereof.

The present invention is also adapted to determine properties of substances, such as: physical parameters, such as the boiling point, refractive index, viscosity, moisture content, rheologic properties and magnetic properties, electrochemical parameters, such as conductivity, pH, oxygen content, permittivity permeability and dielectric constant, chemical properties, such as chemical concentration and identity of the composition and any combination thereof and biological properties, such as bacteria, mold, fungi, alga, virus, microorganisms, eukaryotes and any combination thereof.

It is one object of the invention to disclose a non-destructive on-line system for detecting a presence of a material in a sample of a substance comprising: an MRI device; a flow conduit encompassed by the tunable RF coil of said MRI device and having an input duct and an output duct; a flow of said sample through said flow conduit; a signal detector for detecting frequency-dependent output signals from said MRI device as a function of a frequency variation of the RF tunable coil within a frequency range of an RF resonant frequency of a standard sample of said substance, and a processing unit, wherein said processing unit is compared to determine and impedance frequency variation from said frequency dependent output signals and at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

It is one object of the invention to disclose the non-destructive on-line system as defined above, wherein said at least one characteristic of said substance is selected from the group consisting of at least one physical characteristic, at least one electrochemical characteristic, at least one chemical characteristic and at least one biological (PPECB) characteristic and any combination thereof.

It is another object of the invention to disclose the non-destructive on-line system as defined above, wherein said at least one characteristic comprises an electrical inductance of said substance.

It is another object of the invention to disclose the non-destructive on-line system as defined above, wherein said at least one characteristic comprises an electrical reactance of said substance.

It is another object of the invention to disclose the non-destructive on-line system as defined above, wherein said frequency range is approximately ±100 MHz of said resonant frequency.

It is another object of the invention to disclose the non-destructive on-line system as defined above, wherein said material comprises water.

It is another object of the invention to disclose the non-destructive on-line system as defined above, wherein said output signal comprises a voltage signal.

It is another object of the invention to disclose the non-destructive on-line system as defined above, wherein said output signal comprises a voltage signal comprises an RF voltage signal.

It is another object of the invention to disclose the non-destructive on-line system as defined above, wherein said processing unit is further configured to optimize a production process of said sample.

It is another object of the invention to disclose the non-destructive on-line system as defined above, wherein the system is adapted to measure and control the sample undergoing a modification, where said modification is selected from the group consisting of a physical modification, biological modification, chemical modification and any combination thereof.

It is another object of the invention to disclose the non-destructive on-line system as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose the non-destructive on-line system as defined above, wherein the system is adapted to measure and to control water pollution by at least one contaminant, where said at least one contaminant is selected from organic contaminants, inorganic contaminants and any combination thereof.

It is another object of the invention to disclose the non-destructive on-line system as defined above, wherein the system is adapted to measure an acidity parameter in a food product.

It is another object of the invention to disclose the non-destructive on-line system as defined above, wherein said physical parameter is selected from the group consisting of boiling point, refractive index, viscosity, moisture content, rheologic properties, magnetic properties.

It is another object of the invention to disclose the non-destructive on-line system as defined above, wherein the electrochemical parameter is selected from conductivity, pH, oxygen content, permittivity permeability, dielectric constant and any combination thereof.

It is another object of the invention to disclose the non-destructive on-line system as defined above, wherein said chemical parameter is selected from the group consisting of chemical concentration and identity of the composition and any combination thereof.

It is another object of the invention to disclose the non-destructive on-line system as defined above, wherein said biological parameter is selected from the group consisting of bacteria, mold, fungi, alga, virus, microorganisms, eukaryotes and any combination thereof.

It is another object of the invention to disclose the non-destructive on-line system as defined above, wherein said sample is further selected from the group consisting of a solid, a solgel, a super-critical solution and any combination thereof.

It is another object of the invention to disclose the non-destructive on-line system as defined above, wherein said material is further selected from the group consisting of water-miscible fluids, water-immiscible fluids, aggregated solutions, dispersions, emulsions, solutions slurry, polymer, solid and powder and any combination thereof.

It is another object of the invention to disclose the non-destructive on-line system as defined above, wherein said solid is selected from the group consisting of nanoparticles, fine powders, flowing solids and any combination thereof.

It is another object of the invention to disclose the non-destructive on-line system as defined above, wherein said processor provides a Smith Chart of said impedance frequency variation as a function of said RF frequency such that said impedance frequency variation is function of the reactance and inductance of fluid sample.

It is another object of the invention to disclose the non-destructive on-line system as defined above, wherein said sample comprises a fluid state. It is another object of the invention to disclose the non-destructive on-line system as defined above, wherein said sample comprises a solid state.

It is another object of the invention to disclose a method for detecting a material in a sample of a substance comprising: providing an MRI device; providing a flow conduit encompassed by the tunable RF coil of said MRI device; providing a flow of said sample through said flow conduit; detecting frequency-dependent output signals from said MRI device as a function of a frequency variation of the RF tunable coil within a frequency range of an RF resonant frequency of a standard sample of said substance, and determining an impedance frequency variation from said frequency-dependent output signals and at least one predetermined MRI operational parameter; determining an RF frequency variation of at least one characteristic of said substance from said impedance frequency variation; comparing said RF frequency variation of said at least characteristic of said substance with an RF frequency variation of a corresponding characteristic of a standard sample of said substance, wherein said comparison determines said material content of said sample.

It is another object of the invention to disclose the method as defined above, wherein said at least one characteristic of said substance is selected from the group consisting of at least one physical characteristic, at least one electrochemical characteristic, at least chemical characteristic and at least one biological (PPECB) characteristic and any combination thereof.

It is another object of the invention to disclose the method as defined above, wherein said at least one characteristic comprises an electrical inductance of said substance.

It is another object of the invention to disclose the method as defined above, wherein said at least one characteristic comprises an electrical reactance of said substance.

It is another object of the invention to disclose the method as defined above, wherein said frequency range is approximately ±100 MHz of said resonant frequency.

It is another object of the invention to disclose the method as defined above, wherein said material comprises water.

It is another object of the invention to disclose the method as defined above, wherein said output signal comprises a voltage signal.

It is another object of the invention to disclose the method as defined above, wherein said voltage signal comprises an RF voltage signal.

It is another object of the invention to disclose the method as defined above, wherein the method further comprising optimizing a production process of said sample.

It is another object of the invention to disclose the method as defined above, wherein the method further comprising measuring and controlling said sample undergoing a modification, where said modification is selected from the group consisting of a physical modification, biological modification, chemical modification and any combination thereof.

It is another object of the invention to disclose the method as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose the method as defined above, wherein the method further comprising measuring and controlling water pollution by at least one contaminant, said at least one contaminant is selected from organic contaminants, inorganic contaminants and any combination thereof.

It is another object of the invention to disclose the method as defined above, wherein the method comprises measuring an acidity parameter in a food product.

It is another object of the invention to disclose the method as defined above, wherein said physical parameter is selected from the group consisting of boiling point, refractive index, viscosity, moisture content, rheologic properties, magnetic properties.

It is another object of the invention to disclose the method as defined above, wherein said electrochemical parameter is selected from conductivity, pH, oxygen content, permittivity permeability, dielectric constant and any combination thereof.

It is another object of the invention to disclose the method as defined above, wherein said chemical parameter is selected from the group consisting of chemical concentration and identity of the composition and any combination thereof.

It is another object of the invention to disclose the method as defined above, wherein said biological parameter is selected from the group consisting of bacteria, mold, fungi, alga, virus, microorganisms, eukaryotes and any combination thereof.

It is another object of the invention to disclose the method as defined above, wherein said sample is further selected from the group consisting of a solid, a sol-gel, a super-critical solution and any combination thereof.

It is another object of the invention to disclose the method as defined above, wherein said material is selected from the group consisting of water-miscible fluids, water-immiscible fluids, aggregated solutions, dispersions, emulsions, solution, slurry, polymer, solid and powder and any combination thereof.

It is another object of the invention to disclose the method as defined above, wherein said solid is selected from the group consisting of nano-particles, fine powders, flowing solids and any combination thereof.

It is another object of the invention to disclose the method as defined above, wherein said method further comprises providing a Smith Chart of said impedance frequency variation as a function of said RF frequency such that said impedance frequency variation is a function of the reactance and inductance of fluid sample.

It is another object of the invention to disclose the method as defined above, wherein said sample comprises a fluid state.

It is another object of the invention to disclose the method as defined above, wherein said sample comprises a solid state.

It is another object of the invention to disclose a non-destructive on-line system for detecting a presence of a material in a sample of a substance comprising: an MRI device; a container encompassed by the tunable RF coil of said MRI device containing said sample; a signal detector for detecting frequency-dependent output signals from said MRI device as a function of a frequency variation of the RF tunable coil within a frequency range of an RF resonant frequency of a standard sample of said substance, and a processing unit, wherein said processing unit is configured to: determine an impedance frequency variation from said frequency-dependent output signals and at least one MRI device operational parameter; determine an RF frequency variation of at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

It is another object of the invention to disclose the system as defined above, wherein said at least one characteristic of said substance is selected from the group consisting of at least one physical characteristic, at least one electrochemical characteristic, at least one chemical characteristic and at least one biological (PPECB) characteristic and any combination thereof.

It is another object of the invention to disclose the system as defined above, wherein said at least one characteristic comprises an electrical inductance of said substance.

It is another object of the invention to disclose the system as defined above, wherein said at least one characteristic comprises an electrical reactance of said substance.

It is another object of the invention to disclose the system as defined above, wherein said frequency range is approximately ±100 MHz of said resonant frequency.

It is another object of the invention to disclose the system as defined above, wherein said material comprises water.

It is another object of the invention to disclose the system as defined above, wherein said output signal comprises a voltage signal.

It is another object of the invention to disclose the system as defined above, wherein said voltage signal comprises an RF voltage signal.

It is another object of the invention to disclose the system as defined above, wherein said processing unit is further configured to optimize a production process of said substance.

It is another object of the invention to disclose the system as defined above, wherein the system is adapted to measure and control a sample undergoing a modification, where said modification is selected from the group consisting of a physical modification, biological modification, chemical modification and any combination thereof.

It is another object of the invention to disclose the system as defined above, wherein said sample is selected from the group consisting of tomato sauce, apple beverage, apple concentrate, potato puree, potato paste, potato sauce, potato beverage, potato concentrate.

It is another object of the invention to disclose the system as defined above, wherein the system is adapted to measure and to control water pollution by at least one contaminant, said at least one contaminant is selected from organic contaminants, inorganic contaminants and any combination thereof.

It is another object of the invention to disclose the system as defined above, wherein the system is adapted to measure an acidity parameter in a food product.

It is another object of the invention to disclose the system as defined above, wherein said physical parameter is selected from the group consisting of boiling point, refractive index, viscosity, moisture content, rheologic properties, magnetic properties.

It is another object of the invention to disclose the system as defined above, wherein said electrochemical parameter is selected from conductivity, pH, oxygen content, permittivity permeability, dielectric constant and any combination thereof.

It is another object of the invention to disclose the system as defined above, wherein said chemical parameter is selected from the group consisting of chemical concentration and identity of the composition and any combination thereof.

It is another object of the invention to disclose the system as defined above, wherein said biological parameter is selected from the group consisting of bacteria, mold, fungi, alga, virus, microorganisms, eukaryotes and any combination thereof.

It is another object of the invention to disclose the system as defined above, wherein said sample is further selected from the group consisting of a solid, a sol-gel, a supercritical solution and any combination thereof.

It is another object of the invention to disclose the system as defined above, wherein said material is selected from the group consisting of water-miscible fluids, water-immiscible fluids, aggregated solutions, dispersions, emulsions, solution, slurry, polymer, solid and powder and any combination thereof.

It is another object of the invention to disclose the system as defined above, wherein said solid is selected from the group consisting of nano-particles, fine powders, flowing solids and any combination thereof.

It is another object of the invention to disclose the system as defined above, wherein said processor provides a Smith Chart of said impedance frequency variation as a function of said RF frequency, such that said impedance frequency variation is a function of the reactance and inductance of fluid sample.

It is still another object of the invention to disclose the system as defined above, wherein said sample comprises a fluid state.

It is another object of the invention to disclose the system as defined above, wherein said sample comprises a solid state.

MRI-Free Non-Destructive On-Line System

It is another object of the invention to disclose an MRI-free (namely a non-magnetic analysis device comprising RF coils) non-destructive on-line system for detecting a presence of a material in a sample of a substance comprising: a flow conduit encompassed by the tunable RF coil and having an input duct and an output duct; a flow of said sample through said flow conduit; a signal detector for detecting frequency-dependent output signals as a function of a frequency variation of the RF tunable coil within a frequency range of an RF resonant frequency of a standard sample of said substance, and a processing unit, wherein said processing unit is configured to: determine an impedance frequency variation from said frequency-dependent output signals and optionally at least one MRI device operational parameter; determine an RF frequency variation of at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

It is another object of the invention to disclose an MRI-free system as defined above, wherein said at least one characteristic of said substance is selected from the group consisting of at least one physical characteristic, at least one electrochemical characteristic, at least one chemical characteristic and at least one biological (PPECB) characteristic and any combination thereof.

It is another object of the invention to disclose an MRI-free system as defined above, wherein said at least one characteristic comprises either an electrical inductance of said substance or an electrical reactance of said substance.

It is another object of the invention to disclose an MRI-free system as defined above, wherein said frequency range is approximately ±100 MHz of said resonant frequency.

It is another object of the invention to disclose an MRI-free system as defined above, wherein said material comprises water.

It is another object of the invention to disclose an MRI-free system as defined above, wherein said output signal comprises either a voltage signal or an FR voltage signal.

It is another object of the invention to disclose an MRI-free system as defined above, wherein said processing unit is further configured to optimize a production process of said sample.

It is another object of the invention to disclose an MRI-free system as defined above, configured to measure and control the sample undergoing a modification, where said modification is selected from the group consisting of a physical modification, biological modification, chemical modification and any combination thereof.

It is another object of the invention to disclose an MRI-free system as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose an MRI-free system as defined above, adapted to measure and to control water pollution by at least one contaminant, where said at least one contaminant is selected from organic contaminants, inorganic contaminants and any combination thereof.

It is another object of the invention to disclose an MRI-free system as defined above, adapted to measure an acidity parameter in a food product.

It is another object of the invention to disclose an MRI-free system as defined above, wherein said physical parameter is selected from the group consisting of boiling point, refractive index, viscosity, moisture content, rheologic properties, magnetic properties.

It is another object of the invention to disclose an MRI-free system as defined above, wherein said electrochemical parameter is selected from conductivity, pH, oxygen content, permittivity permeability, dielectric constant and any combination thereof.

It is another object of the invention to disclose an MRI-free system as defined above, wherein said chemical parameter is selected from the group consisting of chemical concentration and identity of the composition and any combination thereof.

It is another object of the invention to disclose an MRI-free system as defined above, wherein said biological parameter is selected from the group consisting of bacteria, mold, fungi, alga, virus, microorganisms, eukaryotes and any combination thereof.

It is another object of the invention to disclose an MRI-free system as defined above, wherein said sample is further selected from the group consisting of a solid, a sol-gel, a super-critical solution and any combination thereof.

It is another object of the invention to disclose an MRI-free system as defined above, wherein said material is further selected from the group consisting of water-miscible fluids, water-immiscible fluids, aggregated solutions, dispersions, emulsions, solution, slurry, polymer, solid and powder and any combination thereof.

It is another object of the invention to disclose an MRI-free system as defined above wherein said solid is selected from the group consisting of nano-particles, fine powders, flowing solids and any combination thereof.

It is another object of the invention to disclose an MRI-free system as defined above, wherein said processor provides a Smith Chart of said impedance frequency variation as a function of said RF frequency such that said impedance frequency variation is function of the reactance and inductance of fluid sample.

It is another object of the invention to disclose an MRI-free system as defined above, wherein said sample comprises either a fluid state or a solid state.

It is another object of the invention to disclose an MRI-free system non-destructive on-line method for detecting a material in a sample of a substance comprising: providing a flow conduit encompassed by the tunable RF coil; providing a flow of said sample through said flow conduit; detecting frequency-dependent output signals as a function of a frequency variation of the RF tunable coil within a frequency range of an RF resonant frequency of a standard s output signals; determining an RF frequency variation of at least one characteristic of said substance from said impedance frequency variation; comparing said RF frequency variation of said at least characteristic of said substance with an RF frequency variation of a corresponding characteristic of a standard sample of said substance, wherein said comparison determines said material content of said sample.

It is another object of the invention to disclose an MRI-free non-destructive on-line system for detecting a presence of a material in a sample of a substance comprising: a container encompassed by the tunable RF coil; a signal detector for detecting frequency-dependent output signals as a function of a frequency variation of the RF tunable coil within a frequency range of an RF resonant frequency of a standard sample of said substance, and a processing unit, wherein said processing unit is configured to: determine an impedance frequency variation from said frequency-dependent output signals; determine an RF frequency variation of at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

BRIEF DESCRIPTION OF THE DRAWINGS

A preferred embodiment of the current invention is described hereinbelow with reference to the following drawings.

DETAILED DESCRIPTION OF PREFERRED EMBODIMENTS OF THE PRESENT INVENTION

Figure 1:
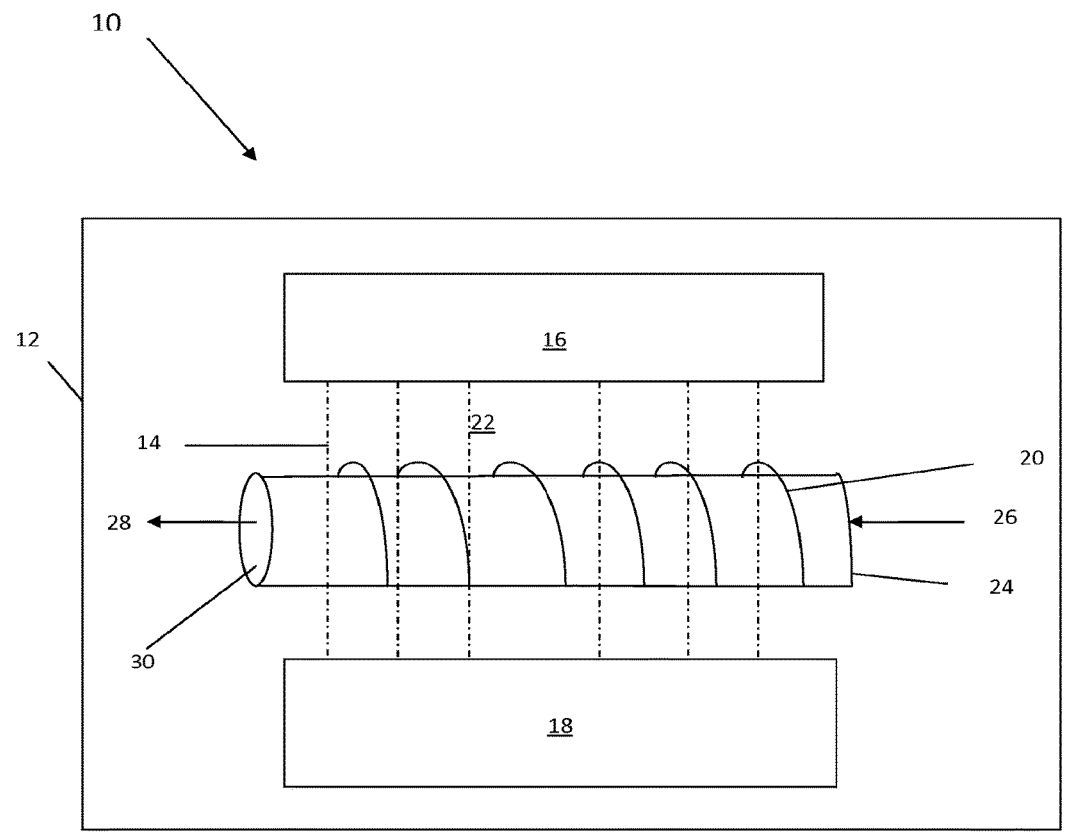
FIG. 1 shows a non-destructive on-line system for detecting a presence of a material in a sample of a substance, in accordance with a preferred embodiment of the present invention.

Reference is now made to FIG. 1, which shows a non-destructive on-line system 10 for detecting a presence of a material in a sample of a substance, in accordance with a preferred embodiment of the present invention. The non-destructive on-line system 10 includes, inter alia, an MRI device 12 for generating a magnetic field 14 between an upper portion 16 and a lower portion 18 of the MRI device 12, as is known in the art. A tunable RF coil 20 encompasses a volume of interest 22 of the MRI device or alternatively MRI-free device 12, as is known in the art.

A flow conduit 24, which is surrounded by the tunable RF coil 20 includes an input duct 26 and an output duct 28. The sample of the substance flows through the flow conduit 24 from the input duct 26 to the output duct 28.

A signal detector 30, including inter alia, an antenna 32 detects RF signals emitted by the MRI device alternatively MRI-free device 12 and demodulates the received signals to obtain MRI output signals, as is known in the art. Typically, the output signals are MRI voltage signals The RF frequency of the RF coil 20 is varied about an RF resonant frequency of the substance, typically, within a frequency range of ±100 MHz of the resonant frequency, such that an RF frequency spectrum is obtained. The from the signal detector 30 are frequency-dependent, V(f).

A processing unit 34 is connected to the signal detector 30 and is configured to determine an impedance frequency variation from the frequency-dependent output voltage signals, V(f), and at least one MRI device parameter. Typically, during the operation of the MRI device alternatively MRI-free device 12, the MRI device alternatively MRI-free device 12 records several operational parameter, such as the output power, (P), of the RF coil as well as the RF current, 1, flowing through the RF coil 20.

Based on the MRI device alternatively MRI-free device operational parameters, the processing unit 34 determines a frequency-dependent impedance of the substance:

$$Z(f)=V(f)/I \qquad (1).$$

It is known in the art, that the impedance of a device, Z, is dependent on the reactance and inductance of the device. In particular:

$$Z(f)=R-j/2\pi fC(f)+2\pi jfL(f) \qquad (2).$$

where R is the resistance, Ω, C is the capacitive reactance, Ω, L is the inductance, H and f is the operating frequency, Hz.

Using a Smith Chart processing code, as is known in the art, the processing unit 34 determines the variation of C(f) and L(f) as a function of the RF frequency.

Figure 2:
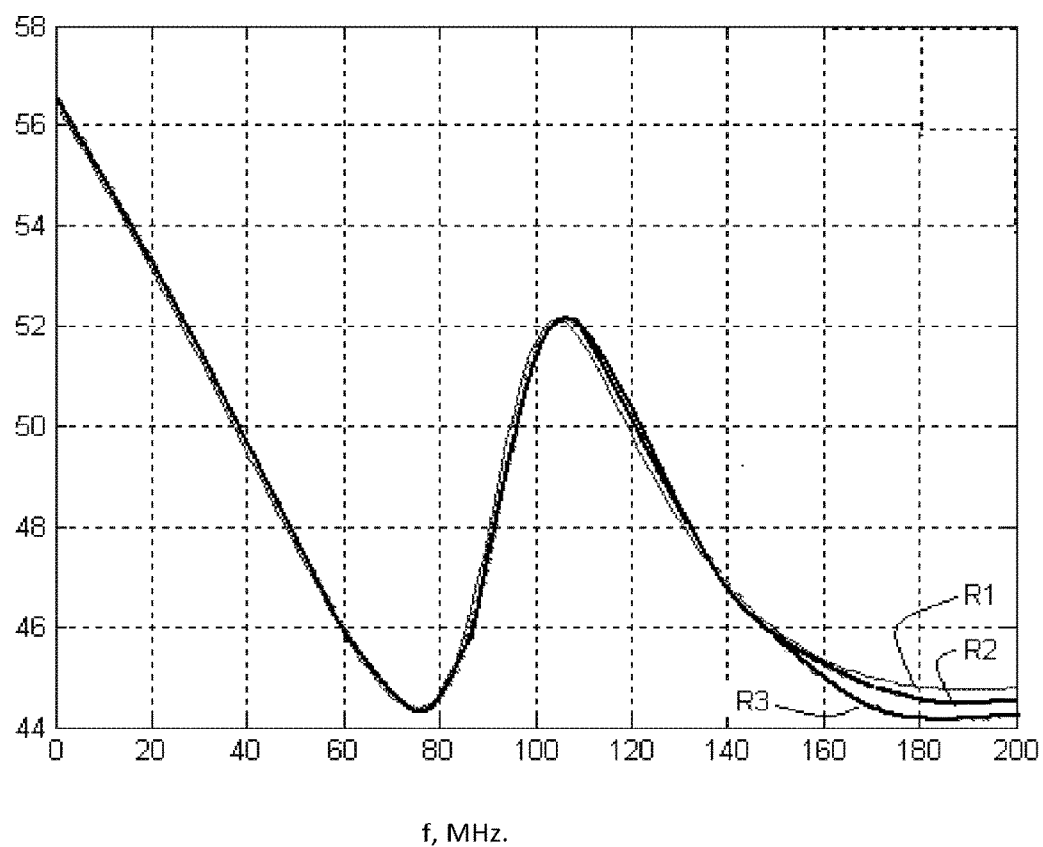
FIG. 2 shows a variation of the reactance C(f) as a function of the RF frequency for a sample of tomato puree, in accordance with a preferred embodiment of the present invention.

Reference is now made to FIG. 2, which shows a variation of the reactance C(f) as a function of the RF frequency, MHz for a sample of tomato puree, in accordance with a preferred embodiment of the present invention. The RF resonant frequency of a standard sample of tomato puree is approximately 100 MHz. FIG. 2 shows the variation of the reactances R1, R2 and R3 for the three samples of tomato puree, sample 1, sample 2 and sample 3, respectively of tomato puree as a function of the RF frequency. Each sample of tomato puree includes different amounts of water. The variation of R1 for as a function of frequency, shows the frequency-dependence reactance variation for a standard sample of tomato puree (sample 1), including one portion of water. The frequency-dependent reactance curves R2 and R3 are for tomato puree including amounts of water different than that of the standard tomato puree. Sample 2 includes a second portion of water and the sample 3 includes a third portion of water.

In FIG. 2, the curves R1, R2 and R3 represent the frequency variations of the reactances of tomato puree for the three samples, sample 1, sample 2 and sample 3, respectively. Differences in the frequency spectrum are discernible at frequencies beyond approximately 150 MHz.

Figure 3:
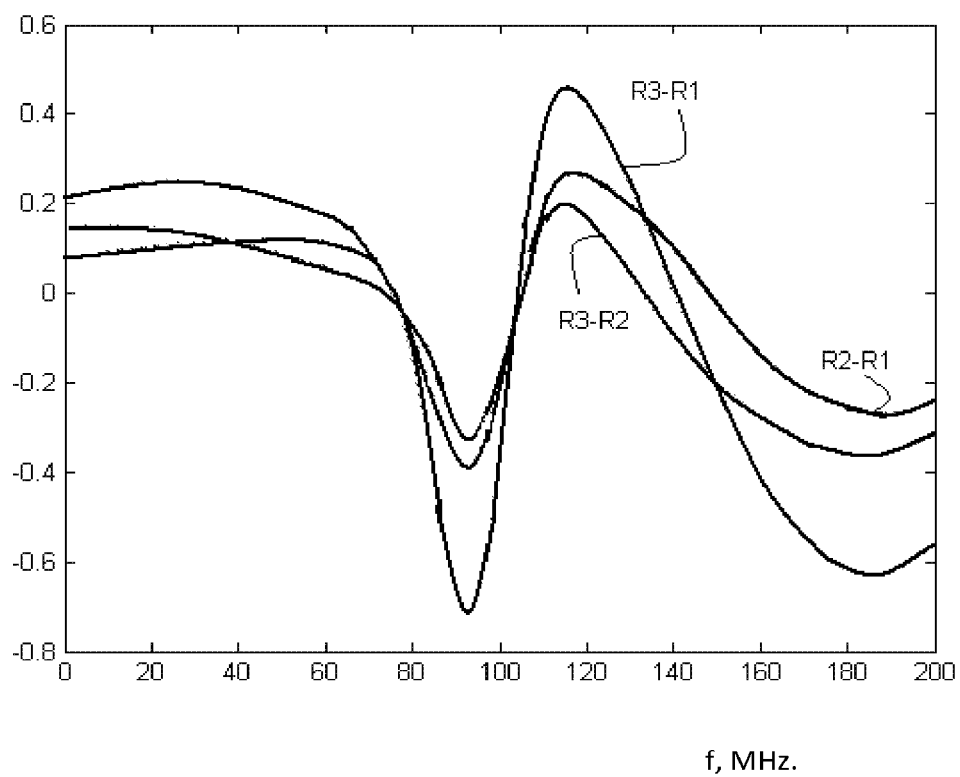
FIG. 3 shows the reactance difference curves for three samples of tomato puree, in accordance with a preferred embodiment of the present invention.

Reference is now made to FIG. 3, which shows the reactance difference curves for the three samples of tomato puree, in accordance with a preferred embodiment of the present invention. FIG. 3 shows the difference curves for the frequency-dependencies of the reactance differences (R3−R1) Ω, (R2−R1) Ω and (R3−R2) Ω, for sample 1, sample 2 and sample 3.

The reactance curves (R3−R1) and (R2−R1) show the reactance frequency variations relative to the reactance of the standard tomato puree, sample 1.

In an MRI-based embodiment, it is known in the art, that the MRI signal is generated by exciting the hydrogen (protons) at RF frequencies and a sample including larger quantities of water generates a larger MRI signal. Therefore, if the puree is diluted with more amounts of water than that of the standard tomato puree, the MRI signal for the diluted purees increases as a function of the amount of water dilution.

FIG. 3 shows the strength of the MRI signal is a function of the amount of water included in the sample. The curves (R3−R1) and (R2−R1) show that the tomato puree sample 2 and tomato puree sample 3, include more water than that of the standard tomato puree sample 1. Furthermore, sample 3 includes more water than sample 2.

Figure 4:
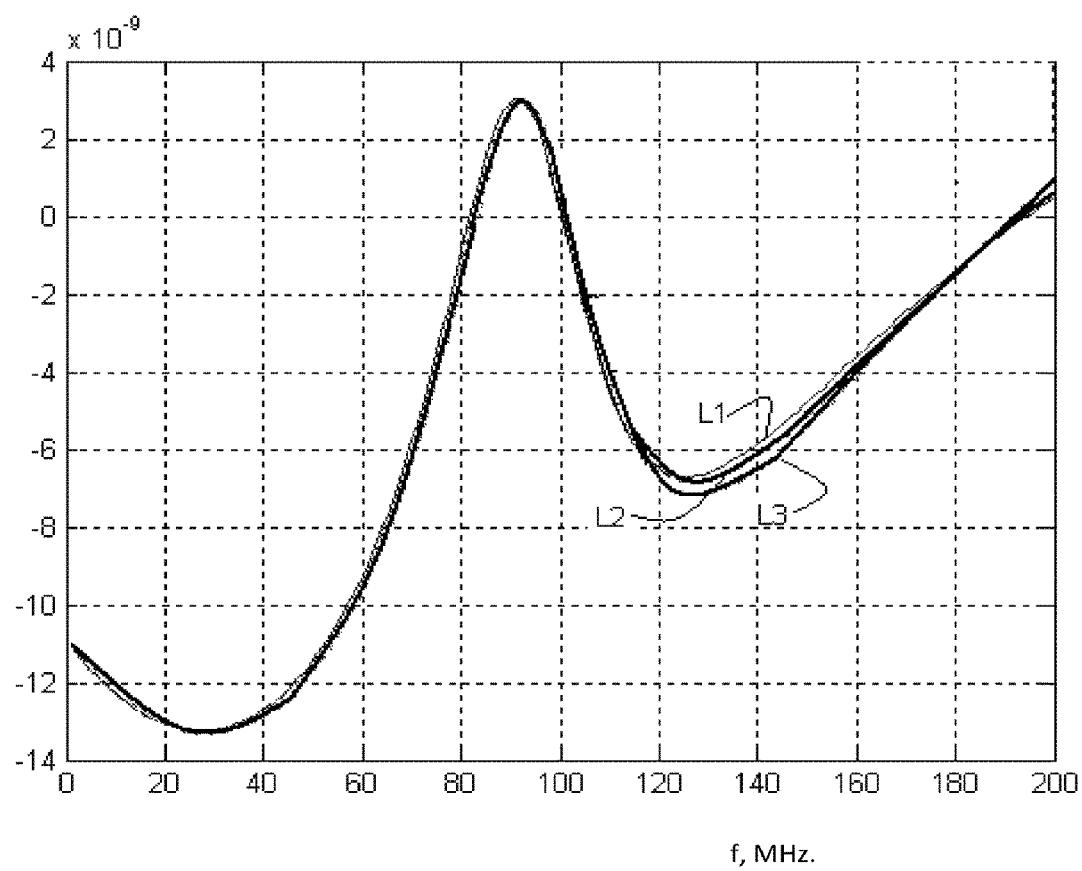
FIG. 4 shows the frequency variation of the inductance for three samples of tomato puree, in accordance with a preferred embodiment of the present invention.

Reference is now made to FIG. 4, which shows the frequency variation of the inductance L for three samples of tomato puree, in accordance with a preferred embodiment of the present invention. As shown in FIG. 4, the differences in the inductance L1, L2 and L3 are discernible in the frequency range of approximately 120-145 MHz.

FIG. 4 shows that the inductance resonance of tomato puree is at approximately 90 MHz.

Figure 5:
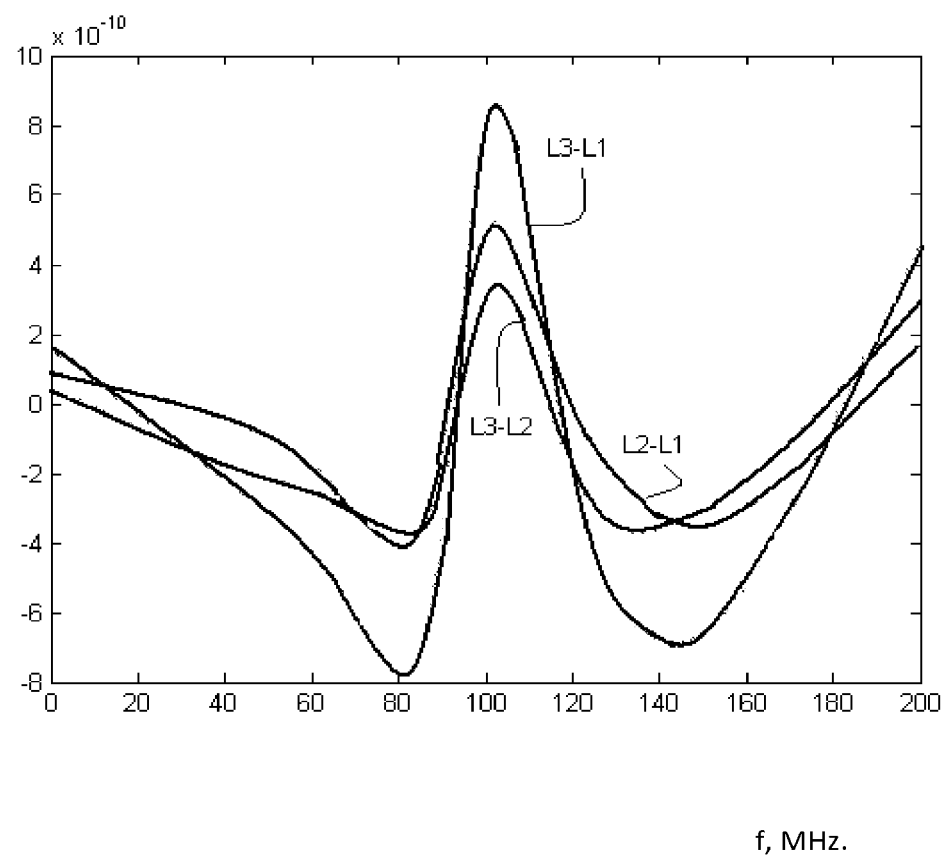
FIG. 5 shows the inductance difference curves for three samples of tomato puree, in accordance with a preferred embodiment of the present invention.

Reference is now made to FIG. 5, which shows the inductance difference curves for the three samples of tomato puree, in accordance with a preferred embodiment of the present invention. FIG. 5 shows the difference curves for the frequency-dependencies of the reactance differences (L3−L1) H, (L2−L1) H and (L3−L2) H, for sample 1, sample 2 and sample 3.

The inductance difference curves (L3−L1) and (L2−L1) show the reactance frequency variations relative to the reactance of the standard tomato puree, sample 1 with inductance the frequency-dependency L1.

FIG. 5 shows the strength of the MRI signal is a function of the amount of water included in the sample. The difference curves (L3−L1) and (L2−L1) show that the tomato puree sample 2 and tomato puree sample 3, include more water than that of the standard tomato puree sample 1. Furthermore, sample 3 includes more water than sample 2.

Thus, using the system shown in FIG. 1 it is possible to test if a sample of a food product fulfills food standard criteria regarding the amounts of water contained therein. It is appreciated that the system of FIG. 1 is also available for determining additional characteristics substance, such as physical, chemical, electrochemical and biological parameters and characteristics of the sample of the substance.

Figure 6:
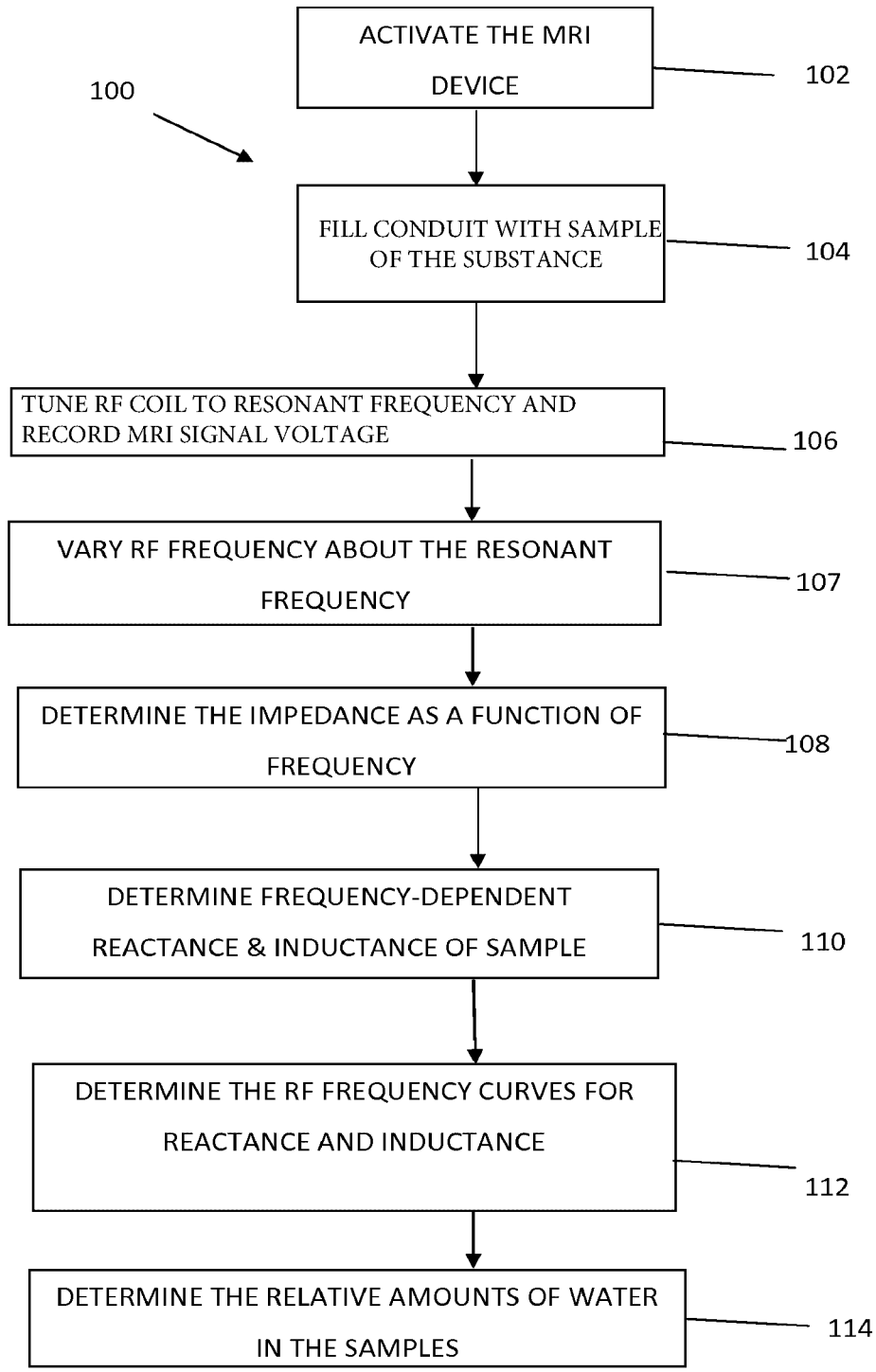
FIG. 6 shows a flow chart for a non-destructive on-line method for detecting a material in a sample of a substance, in accordance with a preferred embodiment of the present invention.

Reference is now made to FIG. 6, which shows a flow chart 100 for a non-destructive online method for detecting a material in a sample of a substance, in accordance with a preferred embodiment of the present invention. In step 102, the MRI device or alternatively MRI-free device 12 is activated and the flow conduit 24 is filled with substance (step 104).

In step 106, the RF coil 20 is tuned to the resonant frequency of the substance and the MRI signal voltage is recorded. In step 107, the RF frequency of the RF coil 20 is varied within a frequency range of ±100 MHz about the resonant frequency and the MRI voltage signal value is recorded at each frequency step.

In step 108, an MRI operational parameter, such as the RF coil current, is recorded from the MRI device's operating parameters and combining this RF current value with the MRI output signal voltage, a variation of the impedance of the sample as a function of the RF frequency is determined.

In step 110, in accordance with equation (2) and the Smith Curve code, as is known in the art, the RF frequency variation of the sample's reactance and inductance are determined. In step 112, the RF frequency difference curves of the sample's reactance and inductance are recorded and in step 114, the amount of water dilution of the sample is determined.

Figure 7:
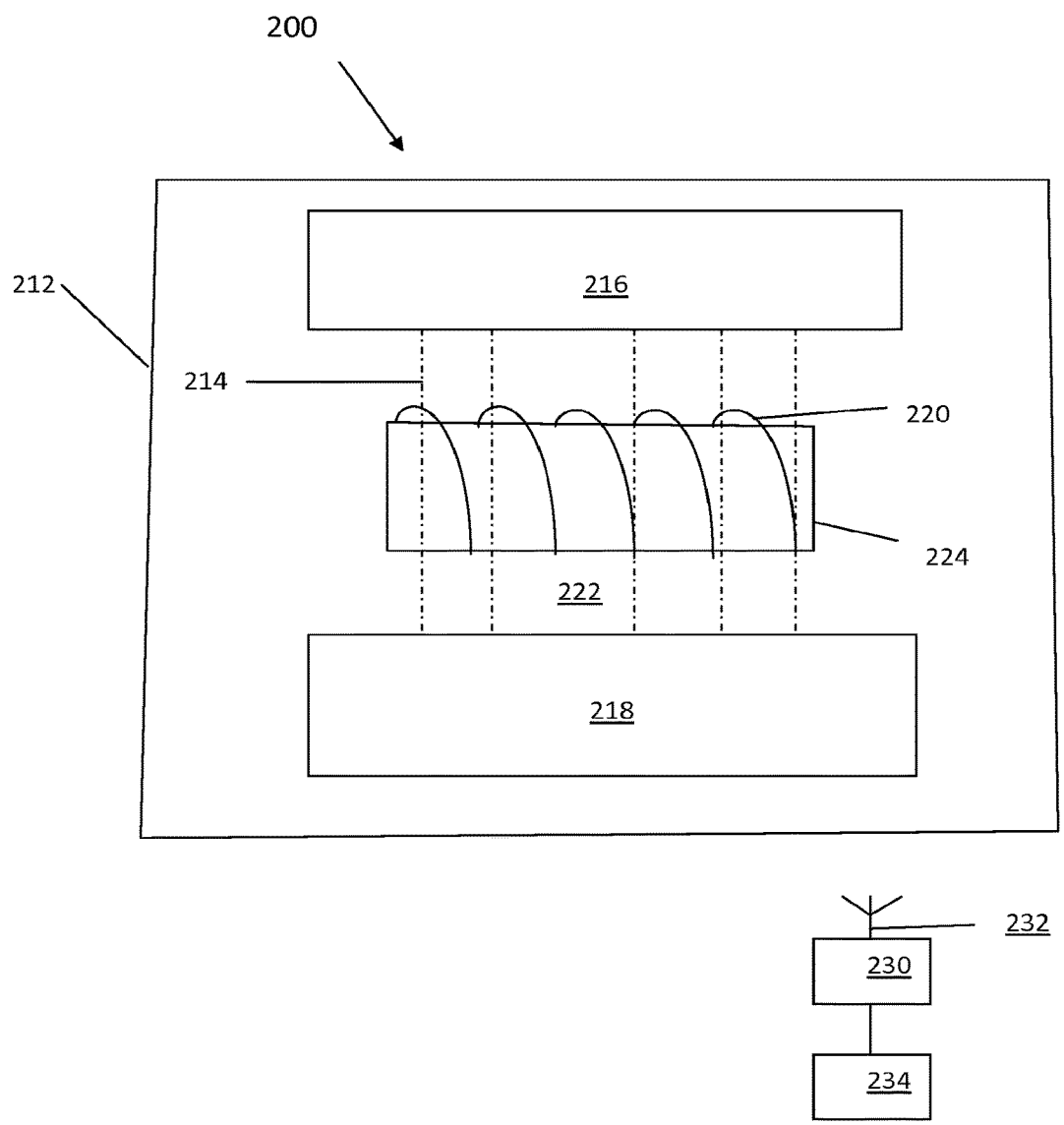
FIG. 7 shows a non-destructive on-line system for detecting a presence of a material in a substance, in accordance with another preferred embodiment of the present invention.

Reference is now made to FIG. 7, which shows a non-destructive on-line system 200 for detecting a presence of a material in a substance, in accordance with another preferred embodiment of the present invention. The non-destructive on-line system 200 includes, inter alia, an MRI device 212 for generating a magnetic field 214 between an upper portion 216 and a lower portion 218 of the MRI device 212, as is known in the art. An tunable RF coil 220 is located in a volume of interest 222 of the MRI device 212, as is known in the art.

A container 224 is encompassed by the tunable RF coil 220 and includes a sample of the substance for testing the amount of water dilution.

A signal detector 230, including inter alia, an antenna 232 detects MRI signals emitted by the MRI device 212 and demodulates the received signals to obtain MRI signals, as is known in the art. Typically, the output signals are MRI voltage signals.

The RF frequency of the RF coil 220 is varied about an RF resonant frequency of the substance, typically, within a fan RF frequency spectrum is obtained. The variation of the RF frequency results in the output voltage signals from the signal detector 230 are frequency-dependent.

A processing unit 234 is connected to the signal detector 230 and is configured to determine an impedance frequency variation from the frequency-dependent output voltage signals, V(f), and at least one MRI device parameter. Typically, during the operation of the MRI device 212, the MRI device 212 records several operational parameters, such as the output power (P), of the RF coil as well as the RF current flowing through the coil, (I).

Based on these parameters, the processing unit 234 determines a frequency-dependent impedance of the sample of substance and the frequency-dependent reactances and inductances, using a Smith Chart processing code, as is known in the art and as described hereinabove. The processing unit 234 determines the variation of C(f) and L(f) as a function of the RF frequency.

EXAMPLES

Below are given various examples which demonstrate the use of the present invention for on-line nondestructive testing. The examples describe the manner and process of the present invention and set forth the best mode contemplated by the inventors for carrying out the invention. These examples are not to be construed as limiting the invention.

Example 1

A water salinity check can be used for homeland security in the event of a spilling a poison, contaminant or chemical in a water reservoir. Although many of the existing detection single devices can detect contaminants at very low concentrations, these devices are often specific to a contaminant or a group of contaminants. Since the physical and chemical properties of contaminants can vary greatly and instruments which check for the existence of a specific contaminant is not useful if the of little use because that contaminant may not be the one used. Most of the biological monitors, such as the use of algae, had limited distribution system. Monitors that use fish or mussels can detect cyanide and chlorinated pesticides, but not at the desired detection limit.

Using the present invention, water from a water-well is pumped through the fluid conduit of the present invention and MRI measurements of the water flow are performed. The MRI signals from the water flow are recorded. The RF frequency of the RF coil is adjusted to the resonance frequency of water and the frequency of the RF coil is adjusted about the resonance frequency. The frequency-dependent reactance and inductance plots for the water flow are determined from a Smith Curve code and the quality of the water flow is monitored. The variation of the reactance and inductance plots from a standard plot enables detection of the water composition change. An alert is activated if the system detects a predetermined significant change.

Example 2

The current invention is operated in a ketchup production line. The MRI device or alternatively MRI-free device is calibrated to the standard resonance frequency of a tomato ketchup. The MRI signals from the ketchup which flow through the flow conduit are optionally recorded. The RF frequency of the RF coil is adjusted to the resonance frequency of the tomato ketchup and the frequency of the RF coil is adjusted about the resonance frequency. The frequency-dependent reactance and inductance plots for the ketchup flow are monitored continuously. On-line information, such as water quantity or water activity, Aw, are also available, enabling either an automatic or manual response to diversions therefrom. Typically, an alert is activated if the system detects a predetermined change, such as 0.5%, in the reactance and/or inductance resonant values. Thus, the amount of water may be increased or decreased to the ketchup according to the customer requirements and preferences.

Example 3

The current invention is operated in an apple puree production line. The MRI device or alternatively MRI-free device is calibrated to the standard resonance frequency of the apple puree. Optionally, the MRI signals from the apple puree flow through the flow conduit are recorded. The RF frequency of the RF coil is adjusted to the resonance frequency of the apple puree and the frequency of the RF coil is adjusted about the resonance frequency. The frequency-dependent reactance and inductance plots for the apple puree flow are monitored continuously. On-line information, such as water quantity or water activity, Aw, are also available, enabling either an automatic or manual response to diversions therefrom. Typically, an alert is activated if the system detects a predetermined change, such as 0.5%, in the reactance and/or inductance resonant values. Thus, the amount of water may be increased or decreased to the apple puree according to the customer requirements and preferences.

Example 4

In the chemical industry it is desired to minimize human exposure to chemicals, such as dangerous chemicals and explosives, for safety reasons and to avoid human error. Using the present invention, it is possible to determine changes in concentration of particular chemicals, such as hydrogen peroxide concentration, in the fluid conduit and determine the diversions from the RF resonant frequency of different chemicals. The current invention performs a correlation, such as a linear correlation, between the reactance and inductance RF frequency resonant values and the determines a percentage of a particular chemical component, for example, hydrogen peroxide, glycol in the process chemical or slurry in the fluid conduit.

Example 5

Using the present invention to provide an automated and non-invasive on-line monitoring of chemical reactions, such as $NaOH+Cl_2 \rightarrow NaOCl+HCL$. The frequency-dependency of the reactances and inductances are determined about the resonant frequency are recorded.

Example 6

The system also provides an automated and non-invasive monitoring of a grain stream. The information of the grain monitoring is used to establish the quality characteristics and the value of the grain. The monitoring is also necessary for proper grain storage management. Information from the grain, such as grain moisture content and the amount of foreign material, can be used to determine appropriate action to maintain the quality of the stored product. The distribution of constituents is generally not uniform throughout the load; the constituents of the grain mass stratify and segregate. This causes variations in the physical characteristics within the load. The air space between the grain constituents causes leaps in the measurement. The method of monitoring is therefore extremely important to ensure that the grain stream is truly representative of the whole grain mass. The frequency per unit volume of grain is measured. A smith chart is measured, and the measurement of the resonant frequency is recorded. The information about the obtained grain moisture is the average moisture of the whole grain mass.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A non-destructive on-line method for detecting a material in a sample of a substance comprising:
   providing a flow conduit encompassed by the tunable radio frequency (RF) coil;
   providing a flow of the sample through the flow conduit;
   detecting frequency-dependent output signals as a function of a frequency variation of a radio frequency (RF) tunable coil have the sample disposed therein, the frequency variation is within a frequency range of an RF resonant frequency of a standard sample of the substance;
   determining an impedance frequency variation from the frequency-dependent output signals;
   determining an RF frequency variation of at least one characteristic of the substance from the impedance frequency variation;
   comparing the RF frequency variation of the at least one characteristic of the substance with an RF frequency variation of a corresponding characteristic of a standard sample of the substance, wherein the comparison determines the material content of the sample.

2. The non-destructive on-line system method of claim 1, wherein the at least one characteristic of the substance is selected from the group consisting of at least one physical characteristic, at least one electrochemical characteristic, at least one chemical characteristic and at least one biological (PPECB) characteristic and any combination thereof.

3. The non-destructive on-line system method of claim 2, wherein the at least one characteristic comprises either an electrical inductance of the substance or an electrical reactance of the substance.

4. The non-destructive on-line method of claim 1, wherein the frequency range is approximately ±100 MHz of the resonant frequency.

5. The non-destructive on-line method of claim 1, wherein the frequency range is approximately from the resonant frequency minus 100 MHz to the resonant frequency plus 100 MHz.

6. The non-destructive on-line method of claim 1, wherein the material comprises water.

7. The non-destructive on-line method of claim 1, wherein the output signal comprises either a direct current (DC) voltage signal or an RF voltage signal.

8. The non-destructive on-line method of claim 1, further comprising optimizing a production process of the sample based on the material content of the sample.

9. The non-destructive on-line method of claim 1, further comprising
   measuring the sample undergoing a modification, the modification is selected from the group consisting of a physical modification, biological modification, chemical modification and any combination thereof; and
   controlling a concentration of the sample based on the measurement.

10. The non-destructive on-line method of claim 1, wherein the substance is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

11. The non-destructive on-line method of claim 1, further comprising controlling water pollution based on measuring at least one contaminant, the at least one contaminant is selected from organic contaminants, inorganic contaminants and any combination thereof.

12. The non-destructive on-line method of claim 1, further comprising measuring an acidity parameter in a food product.

13. The non-destructive on-line method of claim 1, wherein the substance is selected from the group consisting of water-miscible fluids, water-immiscible fluids aggregated solutions, dispersions, emulsions, solution, slurry, polymer, solid and powder and any combination thereof.

14. The non-destructive on-line method of claim 1, wherein the processor provides a Smith Chart of the impedance frequency variation as a function of the RF frequency and wherein the RF frequency variation of inductance and the RF variation of reactance are determined by use of the Smith Chart.

15. The non-destructive on-line method of claim 1, wherein the sample comprises either a fluid state or a solid state.

16. The non-destructive on-line method of claim 2, wherein the physical characteristic is selected from the group consisting of boiling point, refractive index, viscosity, moisture content, rheologic properties, magnetic properties.

17. The non-destructive on-line method of claim 2, the electrochemical characteristic is selected from conductivity, pH, oxygen content, permittivity permeability, dielectric constant and any combination thereof.

18. The non-destructive on-line according to claim 2, wherein the chemical parameter is selected from the group consisting of chemical concentration and identity of the composition and any combination thereof.

19. The non-destructive on-line according to claim 2, wherein the biological parameter is selected from the group consisting of bacteria, mold, fungi, alga, virus, microorganisms, eukaryotes and any combination thereof.

20. The non-destructive on-line according to claim 2, wherein the sample is further selected from the group consisting of a solid, a sol-gel, a super-critical solution and any combination thereof.

* * * * *